United States Patent [19]

Pronovost et al.

[11] Patent Number: 5,424,193
[45] Date of Patent: Jun. 13, 1995

[54] ASSAYS EMPLOYING DYED MICROORGANISM LABELS

[75] Inventors: Allan D. Pronovost; Gerald L. Rowley, both of San Diego, Calif.

[73] Assignee: Quidel Corporation, San Diego, Calif.

[21] Appl. No.: 23,670

[22] Filed: Feb. 25, 1993

[51] Int. Cl.⁶ ............... G01N 33/543; G01N 33/554; G01N 33/558

[52] U.S. Cl. .................... 435/7.32; 422/55; 422/56; 435/7.33; 435/805; 435/806; 435/883; 435/970; 435/971; 436/501; 436/510; 436/514; 436/518; 436/519; 436/807; 436/810; 436/814; 436/818; 436/828

[58] Field of Search ............... 435/7.32–7.34, 435/7.92–7.94, 805–806, 883, 849, 885, 970, 971, 972; 436/518, 519, 510, 65, 807, 810, 814, 818, 501, 514, 828; 422/55–56

[56] References Cited

U.S. PATENT DOCUMENTS

| | | | |
|---|---|---|---|
| 1,816,026 | 7/1931 | Schaffer | 436/519 |
| 2,301,717 | 11/1942 | Terry | 436/519 |
| 3,553,310 | 1/1971 | Csizmas et al. | 436/519 |
| 3,562,384 | 2/1971 | Arquilla | 436/519 |
| 4,166,105 | 8/1979 | Hirschfeld | 436/800 X |
| 4,169,138 | 9/1979 | Jonsson | 424/12 |
| 4,313,734 | 2/1982 | Leuvering | 436/525 |
| 4,373,932 | 2/1983 | Gribnau et al. | 436/501 |
| 4,433,059 | 2/1984 | Chang et al. | 436/512 |
| 4,452,886 | 6/1984 | Henry | 435/7 |
| 4,508,829 | 4/1985 | Sulitzeanu | 436/519 X |
| 4,608,246 | 8/1986 | Bayer et al. | 424/11 |
| 4,639,419 | 1/1987 | Olson et al. | 436/519 X |
| 4,703,017 | 10/1987 | Campbell et al. | 436/501 |
| 4,711,841 | 12/1987 | Kronvall | 436/519 X |
| 4,745,075 | 5/1988 | Hadfield et al. | 436/523 X |
| 4,863,875 | 9/1989 | Bailey et al. | 436/518 |
| 4,920,046 | 4/1990 | McFarland et al. | 436/519 X |
| 4,943,522 | 6/1990 | Eisinger et al. | 435/7 |
| 5,063,151 | 11/1991 | Kuehn et al. | 436/519 X |
| 5,079,170 | 1/1992 | Rosman et al. | 436/178 |
| 5,145,789 | 9/1992 | Corti et al. | 436/530 |
| 5,236,846 | 8/1993 | Senyel et al. | 436/518 X |
| 5,308,775 | 5/1994 | Donovan et al. | 436/518 |

FOREIGN PATENT DOCUMENTS 276152 7/1988 European Pat. Off. .
2204398 11/1988 United Kingdom .

OTHER PUBLICATIONS

Jonsson et al. "The Use of Protein A-containing Staphylococcus arueus as a Solid Phase Anti-IgG reagent in Radioimmunoassays as Exemplified in the Quantitation of α-fetoprotein in Normal Human Adult Serum", *Eur. J. Immunol.* 4:29–33 (1974).

Guesdon et al., "Lectin Immuno Tests: Quantitation and Titration of Antigens and Antibodies Using Lectin-Antibody Conjugates", *J. Immunol. Meth.* 39:1–13 (1980).

J. Prévot et al. Ann. Virol. (1981) 132 E. 529–542.

*Primary Examiner*—David Saunders
*Attorney, Agent, or Firm*—Townsend and Townsend Khourie and Crew

[57] ABSTRACT

The present invention relates generally to test articles and assays for the detection of analytes in biological fluid samples. More particularly, the present invention relates to test articles an assays which employ dyed microorganisms as visual labels to detect suspected analytes.

34 Claims, 1 Drawing Sheet

ASSAYS EMPLOYING DYED MICROORGANISM LABELS

BACKGROUND OF THE INVENTION

1. Field of the Invention

The present invention relates generally to test articles and assays for the detection of analytes in biological fluid samples. More particularly, the present invention relates to test articles and assays which employ dyed microorganisms as visual labels to detect the suspected analytes.

The use of chromogenic and fluorescent dyes as "labels" in biological assay procedures is known. Typical assay protocols call for direct or indirect binding of a dye label to an analyte or analyte analog in a biological sample, where the presence or absence of the dye at a particular stage of the assay can be determined visually and related to the amount of analyte initially present in the sample. A wide variety of specific assay protocols exist.

Of particular interest to the present invention, certain assays utilize naturally colored or dyed particles as a label, where the particles are bound to an antibody or other specific binding substance. Suggested particles include dyed latex beads, dye imbibed liposomes, erythrocytes, metal sols, and the like. The colored particle in such complexes can serve as a visible marker, where separation, capture, or aggregation of the particles is mediated through binding of the antibody or other specific binding substance. The amount of label thus segregated in a particular assay step is related to the amount of analyte initially present in the sample.

A variety of methods for preparing such antibody-particle compositions have been proposed. Such methods generally rely on producing a colored particle, typically by dying a latex bead, a liposome, or the like, and subsequently attaching the colored particle to the antibody, typically by passive adsorption or by covalent binding.

While generally useful, methods for preparing such antibody-particle compositions can be relatively complex, usually requiring multi-stage operations including preparation of the particle, coloring of the particle, attachment of the particle to the antibody, and blocking of the particle for use in immunoassays. Some particles, such as liposomes, are relatively unstable and do not provide uniform characteristics following storage or during use in some samples. Moreover, a loss of antibody binding capacity can often result from the particle attachment. Sometimes these particles are not compatible with the antibodies selected for a particular application. Often times the antibodies are bound to the particle inefficiently and without regard to orientation for maximal immunological reactivity.

It would be desirable to provide improved labeling compositions that would allow for antibodies of any specificity to be used for an application. The compositions should be relatively easy to prepare, with a reduced cost, and have uniform characteristics. In particular, the compositions should retain antibody activity to a significant extent with proper antibody orientation, i.e. Fc region bound, and be very stable during storage and under assay conditions to provide for long product shelf life. It will be appreciated, however, that the methods and compositions of the present invention need not be superior to the prior art in each or any of these aspects, but rather that these are general advantages that the present invention can provide relative to certain prior art methods and products.

2. Description of the Background Art

U.S. Pat. No. 4,943,522, describes a solid phase lateral flow assay using erythrocytes as a label. U.S. Pat. No. 4,863,875, describes compositions comprising at least ten dye molecules or monomers covalently attached to an antibody through an isocyanate group on the dye. U.S. Pat. No. 4,861,711, describes a solid phase lateral flow assay using enzyme antibody conjugate and substrate, each separately held in absorbent pads. U.S. Pat. No. 4,703,017, describes a solid phase assay device which relies on specific binding of a ligand-label conjugate on a solid support, where the label is disclosed as a particle, such as, i.e., a liposome, or polymer microcapsule. U.S. Pat. No. 4,608,246 describes assays for typing blood which employ erythrocytes as a labelling agent. U.S. Pat. No. 4,452,886, describes the covalent attachment of photon absorbing or emitting polymers to proteins, such as antibodies and antigens. U.S. Pat. No. 4,373,932, describes labeling of a ligand with an aqueous dispersion of a hydrophobic dye or pigment, or a polymer nuclei coated with such a dye or pigment. U.S. Pat. No. 4,313,734 describes methods of detecting sample analytes by the determination of the metallic label content in the sample. U.S. Pat. No. 4,169,138 describes immunoassays which employ visible particles including undyed microorganisms, bound to polymers which may be of microbial origin. See also, U.K. Patent No. 2,204,398; EP Patent No. 306 722; and EP Patent No. 276 152, which relate to lateral flow assays.

Enzyme assays and immunohistochemical staining techniques which produce a colored dye by reaction of a substrate with an enzyme bound to a target moiety are known. Jonsson et al., *J. Immunol.*, 4:29–33, describes a radioimmunoassay employing *Staphylococcus aureus* bacteria as a solid phase for separation of IgG-antigen complexes from free antigen. Leuvering and Van de Waart, *J. Immunoassay*, 1:77–91, describes immunoassays employing inorganic sol particles as labels. Guesdon and Avraneas, *J. Immunol. Meth.*, 39:1–13, and Prenot and Guesdon, *Ann. Virol.*, 132:529–542, describe immunoassays employing erythrocytes as the labelling composition.

SUMMARY OF THE INVENTION

The present invention provides test articles which comprise a support matrix, and a labelling complex impregnated within the support matrix, wherein the labelling complex comprises a dyed microorganism having a specific binding substance on its cell surface.

One embodiment of the present invention provides a test device for lateral flow assays which comprises a support matrix defining a flow path; a sample receiving zone located along said flow path and having a binding substance specific for analyte impregnated therein; a labelling zone located along said flow path downstream from said sample receiving zone and having a labelling complex impregnated therein, wherein said labelling complex comprises a dyed microorganism having a binding substance specific for said analyte-specific binding substance on its cell surface; and a capture zone located along said flow path downstream from said labelling zone and having a binding substance specific for said analyte immobilized therein.

Other aspects of the claimed invention are methods for preparing test devices in which labelling complexes comprised of dyed microorganisms having a labelling binding substance on its cell surface are impregnated within a support matrix.

Also provided are lateral flow assays, in both non-competitive and competitive format wherein binding between a labelling complex, consisting essentially of a dyed microorganism having a specific labelling binding substance on its cell surface, and a capture binding substance within a capture zone is mediated by the presence of an analyte in a sample flowing through said capture zone, in which binding between the labelling complex and the capture binding substance is effected directly or indirectly through the cell surface specific labelling binding substance.

DETAILED DESCRIPTION OF SPECIFIC EMBODIMENTS

Figure 1:
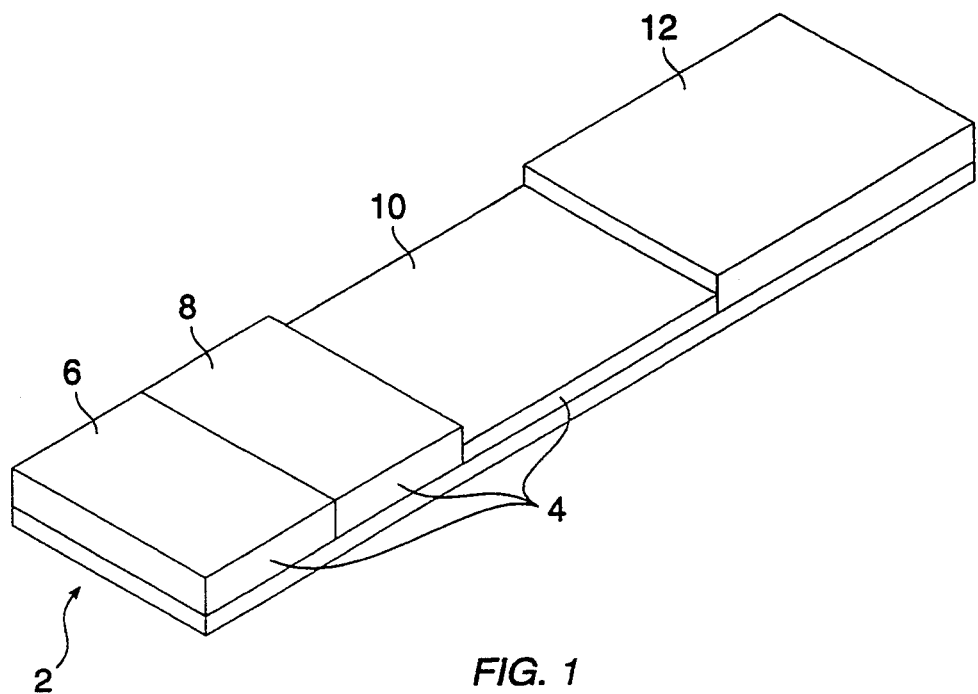
FIG. 1 illustrates a test article constructed in accordance with principles of the present invention.

The present invention provides test articles and assays for use in detecting analytes in biological fluid samples. The test articles and assays employ dyed microorganisms within labelling complexes which allow identification of the analyte in the sample. The labeling complexes are visually discernable and capable of providing a readily apparent color signal when aggregated or accumulated in a capture zone as described in more detail hereinafter. While use of dyed microorganisms is particularly valuable for use in lateral flow assay protocols and lateral flow assay devices, dyed microorganisms are also useful in a wide variety of other assay formats such as described by U.S. Pat. No. 5,079,170, incorporated herein by reference.

Lateral flow assay techniques are generally described in U.S. Pat. Nos. 4,943,522; 4,861,711; 4,168,146; 4,094,647; 4,235,601; 4,361,537; 4,857,453; 4,703,017; 4,855,240; 4,775,636; copending application U.S. Ser. No. 07/639,967, European Patent Application No. 451,800; 158,746; 276,152 (now abandoned); 306,772 and British Patent Application No. 2,204,398; each of which is incorporated herein by reference.

The present invention provides test articles and methods which are useful for the detection or quantitation of analytes in biological fluid samples. A wide variety of analytes, such as human chorionic gonadotropin (hCG), prostate specific antigen (PSA), carcinoembryonic antigen (CEA), antigen-specific immunoglobulins, and the like may be detected by the present invention. The biological fluid samples may include serum, whole blood, urine, sputum, saliva, sweat, plasma and the like. Herein, fluid homogenates of cellular tissues are also considered biological fluids.

Generally, the test articles of the present invention comprise a support matrix having a labelling complex impregnated therein. As used hereinafter, "impregnated" is meant to refer to a state of permeation or reversible surface adherence. Substances which are impregnated are not immobilized within or upon the support matrix, but are capable of being mixed or suspended in fluids placed on the support matrix.

The support matrix of the test article may be capable of non-bibulous lateral flow. By "non-bibulous lateral flow" is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

A typical non-bibulous material suitable for use as a support matrix is high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. The optimum pore diameter for the membrane for use in the invention is about 10 to about 50 $\mu$m. The membranes typically are from about 1 mil to about 15 mils in thickness, typically in the range of from 5 or 10 mils, but may be up to 200 mils and thicker. The membrane may be backed by a generally water impervious layer, such as mylar. When employed, the backing is generally fastened to the membrane by an adhesive, such as 3M 444 double-sided adhesive tape. Typically, a water impervious backing is used for membranes of low thickness. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used.

Bibulous materials, such as untreated paper, cellulose blends, nitrocellulose, polyester, an acrylonitrile copolymer, rayon, glass fiber, and derivatized nylon and the like may also be employed as support matrix materials to provide either bibulous or non-bibulous flow. To provide non-bibulous flow, these materials may be treated with blocking agents that may block the forces which account for the bibulous nature of bibulous membranes. Suitable blocking agents include bovine serum albumin, whole animal serum, casein, and non-fat dry milk.

Typically, the support matrix will define a flow path. The flow path is generally lateral, although other configurations are acceptable and may be preferred for some embodiments. For example, circular or radial flow paths are particularly useful for test devices which can simultaneously detect the presence of multiple analytes in a sample such as screening for immunoglobulins specific for *Toxoplasma gondii*, Rubella virus, Cytomegalovirus, Herpes simplex virus, *Chlamydia trachomatis*, and *Treponema pallidum* or for allergen-specific antibody detection.

The support matrix will often be divided into different zones: the sample receiving zone, the labelling zone and the capture zone. The support matrix may be composed of different membranes in the different zones of a single test article. For example, zones of different porosity may be desired to provide a filtering function in the sample receiving zone and non-bibulous flow in the downstream zones. Other combinations may be desired for particular uses.

The sample accepting zone provides a means for applying the sample to test articles of the present invention. In some embodiments, the sample receiving zone will have a low analyte retention rate. Treatment of the sample receiving zone to immobilize a protein-blocking reagent on the surface will typically provide low retention properties. This treatment also provides increased wetability and wicking action to speed the downstream flow of the serum sample. The sample receiving zone may also serve as a means for filtering particulates from the sample.

Typically, the sample receiving zone will be impregnated with an analyte binding substance. The analyte binding substance may be dried or lyophilized once impregnated into the sample accepting zone. The analyte binding substance is a compound which will selectively bind the suspected analyte. By "selectively bind", it is meant that the analyte binding substance will have a greater affinity for the analyte than other compounds in the fluid sample. The binding will generally, but not necessarily, be non-covalent.

Typically, the analyte binding substance will be an antibody which is specific for the analyte to be detected or measured. Either monoclonal antibodies or antigen-specific polyclonal antibodies may be employed. Many analyte-specific antibodies are commercially available. Alternatively, persons of skill may readily prepare antibodies to analytes of interest by methods well known in the art. See, e.g., Harlow and Lane, "Antibodies, A Laboratory Manual" Cold Spring Harbor Laboratory, Cold Spring Harbor N.Y. (1988), incorporated herein by reference.

Other analyte binding substances may also be employed. Conveniently, naturally occurring substances which are anti-ligands of the analyte may be available. For example, when measuring a hormone such as hCG, purified hCG receptor, or binding fragments thereof, may be the analyte binding substance specific for the analyte. Persons of skill will readily appreciate appropriate binding substances for particular analytes.

When the fluid sample is placed on a sample receiving zone impregnated with analyte binding substances, the analyte binding substances mix in the fluid sample. The mixing results in analyte present in the sample contacting the binding substances and forming an analyte/binding substance complex. The fluid containing the analyte/binding substance complexes is channeled downstream by the flow path of the solid support matrix.

A labelling zone may be located along the flow path of the support matrix downstream from the sample accepting zone. Labelling complexes are impregnated in the labelling zone. The labelling complexes are comprised of a dyed microorganism having a cell surface labelling binding substance specific for the analyte/binding substance complex. As the analyte/binding substance complexes flow into the labelling zone, the labelling complexes are mixed in the fluid sample. The labelling binding substance binds to the conjugates thereby linking the dyed microorganism to the analyte. Generally, the labelling complexes are dried or lyophilized following impregnation within or upon the labelling zone.

Dyed microorganisms have a variety of advantages over labels previously employed in the art. The microorganisms are naturally occurring and easy to produce. No complex chemical synthesis, such as that needed for liposome production, is required. Microorganisms can be dyed with a wide variety of compounds which are well known in the art. Microorganisms have many amino group-containing proteins for dying. Killed microorganisms are also stable under conditions of drying or lyophilization which are convenient methods of test device preparation and preservation. Some forms of microorganisms are inherently very stable, i.e. Candida. Some microorganisms, such as *Staphylococcus aureus* and Groups C or G Streptococcus, have naturally occurring cell surface constituents which may naturally serve as labelling binding substances.

A variety of microorganisms, such as *Staphylococcus aureus*, Group C or G Streptococcus, *Escherichia coli*, *Candida albicans*, or other unicellular procaryotes or eukaryotes may be used in the present invention. The choice of microorganism may be determined by the natural presence of cell surface specific binding proteins (e.g., Staphylococcal Protein A or Protein G) which can function as labelling binding substances. Other factors which may influence the choice of microorganism are the relative size of the microorganism compared with the pore size of the support matrix, the color density required by the assay which can be altered by available amino group density of naturally occurring labelling binding substances, and the like.

The microorganisms may be cultured as appropriate for the organism by means well known in the art. Generally, the microorganisms will be killed prior to being dyed to produce colored microorganisms.

The organisms may be dyed by a variety of means. Gram staining is a well known and acceptable method for staining bacteria. Other acceptable dyes include Cibacron Brilliant Red 3B-A, Remazol Brilliant Blue R, Reactive Orange 16, Reactive Blue 4, and Reactive Black 4, each of which is available from Aldrich, Milwaukee, Wis. and other sources. Dying organisms with these dyes is generally accomplished in basic buffers such as sodium bicarbonate sodium carbonate solutions. The buffer may be adjusted to the desired pH.

The dyed microorganisms of the labelling complex may have a cell surface labelling binding substance specific for the analyte/binding substance conjugate. The labelling binding substance may be specific for an exposed region of the analyte, the analyte binding substance, or a structure formed by the conjugation. For example, if the analyte binding substance is a natural receptor of the analyte, the labelling binding substance may be an antibody specific for an epitope of the receptor which is distant from the hormone binding site. The cell surface labelling binding substance may also be an antibody specific for the analyte binding substance. Following dying of the microorganism, the antibody may be chemically attached to the microorganism by a coupling agent.

Conveniently, but not exclusively, the labelling binding substance may be a compound which is naturally present on the microorganism's cell surface. For example, Staphylococcal Protein A (SPA) is naturally present on many strains of *Staphylococcal aureus*. SPA has multiple binding sites for the Fc regions of antibody molecules which do not encroach on the antibody's antigen binding sites. Thus, SPA can bind analyte specific antibodies and link the analyte/binding substance conjugate to the dyed *Staphylococcus aureus* when the analyte binding substance is an antibody.

Another naturally occurring cell surface labelling substance is Protein G. Protein G is present in the cell walls of Group C and G β-hemolytic Streptococci. Like SPA, Protein G has a high natural affinity for antibody molecules which provides for selective binding.

Antibodies which specifically bind the dyed microorganisms may also be used as labelling binding substances when complexed with SPA or other antibody binding compounds. Because SPA has multiple antibody binding sites, it may bind to both the microorganism-specific antibody and analyte specific antibodies employed as analyte binding substances. The antibody/SPA conjugate then links the dyed microorganism with the analyte. Other labelling binding substances will be appreciated by those of skill in the art.

Alternatively, the dyed microorganisms may be derivatized with specific functional groups to allow for the covalent attachment of antibodies or other analyte-specific binding substances using homo- or heterobifunctional coupling reagents (available from Pierce, Rockford, Ill.) to attach these analyte binding substances to the dyed microorganisms.

The support matrix also contains a capture zone. A capture binding substance which is specific for the analyte will be immobilized in the capture zone. Typically, an anti-analyte immunoglobulin is the capture binding substance. If the labelling binding substance specifically binds antibodies, such as SPA or Protein G, only antibody binding fragments lacking the Fc region (e.g., Fab or F(ab)$_2$ fragments) may be employed as the capture binding substances. Otherwise, dyed microorganisms may be retained by binding between the labelling binding substance and the Fc region of the immobilized capture binding substance.

The accumulation of visible microorganism label may be assessed either visually or by optical detection devices, such as reflectance analyzers and video image analysis and the like. The accumulation of visible label can be assessed either to determine the presence or absence of label in the capture zone or the visible intensity of accumulated label which may by correlated with the concentration of analyte in the biological sample. The correlation between the visible intensity of accumulated label and analyte concentration may be made by comparison of the visible intensity to a reference standard which may or may not be incorporated into the capture zone. Optical detection devices may be programmed to automatically perform this comparison by means similar to that used by the Quidel Reflective Analyzer, Catalog No. QU0801 (Quidel Corp., San Diego, Calif.). Visual comparison is also possible by visual evaluation of the intensity and a color key such as used in the Quidel Total IgE Test Catalog No. 0701 (a multi-step ELISA assay). Thus, analyte concentration may be determined by the present invention.

The capture zone is often contacted by a bibulous absorbent zone. The absorbent zone is located downstream from the capture zone. The absorbent zone is a means for removing excess sample and unbound labelling complexes from the matrix of the device. Generally, the absorbent zone will consist of an absorbent material such as filter paper, a glass fiber filter, or the like and may contain end of assay indicators that indicate the time at which the assay is over or can be read at the beginning and/or end of a time read period.

The embodiments of the present invention which employ a lateral flow assay format provide a means for one-step or multi-step detection and/or quantitation of the analyte. Generally, the biological fluid sample is placed on the sample receiving zone. The analyte binding substance impregnated in the support matrix mixes with the fluid sample. Analyte present in the fluid sample then binds the analyte binding substance forming an analyte/binding substance conjugate.

The conjugate is carried by the lateral flow of the fluid to the labelling zone. The labelling complexes impregnated therein mix with the fluid. The labelling binding substance of the labelling complexes binds conjugate in the fluid forming a labelled conjugate. The labelled conjugates are carried to the capture zone by the lateral flow of the fluid. The labelled conjugates comprise an analyte-analyte binding substance-labelling binding substance-dyed microorganism structure which links analyte present in the fluid sample to the dyed microorganism which serves as the label.

The labelled conjugates contact the capture zone which contains immobilized capture binding substances which specifically bind analyte. The analyte-containing labelled conjugates are retained in the capture zone by binding between the analyte and the capture binding substance thereby concentrating the dyed microorganisms in the capture zone. The dyed microorganisms thus retained provide a visual means to detect analyte present in the serum.

Another embodiment of the present invention provides non-lateral flow assays for determining the presence of an analyte in a sample, said assay comprising a means for capturing the analyte and a means for labelling captured analyte, wherein the improvement comprises a labelling complex consisting essentially of a dyed microorganism having a specific labelling binding substance on its cell surface wherein capture of the labelling complex by the capture means is mediated directly or indirectly through the cell surface labelling binding substance. The choice of dyed microorganism is not critical and may vary. Typically, *Staphylococcus aureus* having cell surface Protein A will be employed.

Assays of this type are generally non-lateral flow membrane-assays. In this type of assay a capture binding substance is immobilized on a porous membrane. The immobilized capture binding substance provides the capture means. The capture binding substance specifically binds the analyte to be detected, but not the labelling complex.

The biological fluid sample is placed on the membrane in contact with the capture binding substance. Analyte in the sample binds the capture binding substance while the remaining sample flows through the membrane. A solution containing labelling complexes is then applied. The labelling complexes bind captured analyte through the labelling binding substances on the microorganism cell surfaces. The labelling complexes are linked to the capture binding substance through the captured analyte and the labelling binding substance. Unbound labelling complexes flow through the membrane. Accumulation of labelling complexes on the membrane is detected by a color change which indicates that the biological fluid sample contains analyte.

Alternatively, test devices constructed in accordance with the principles of the present invention may employ a competitive binding format. Labelling complexes bound to analyte may be reversibly bound to the capture binding substances in the capture zone. If analyte is present in the biological fluid sample, the labelling complexes will be displaced from the capture binding substances and the color intensity of the capture zone will decrease as the fluid sample contacts the capture zone. The color change can be compared to reference standards to determine the analyte concentration in the sample.

When preparing test devices for competitive assays, the capture binding substances immobilized on the support matrix should be exposed to an excess of labelling complexes bound to analyte. In this manner, binding sites of the capture binding substances will be saturated with label and analyte in the biological fluid will only bind to capture binding substance from which the labelling complexes have been displaced.

Referring now to FIG. 1, a test article 2 constructed in accordance with the principles of the present invention is illustrated. The test article 2 will employ a non-bibulous support matrix 4 and a lateral flow format. Persons of skill will appreciate that other devices employing different assay formats, bibulous support matrixes, and other modifications may be constructed for use with the dyed microorganism labels of the present invention.

The support matrix 4 is capable of receiving biological fluid samples and conducting the samples in a lateral direction. The support matrix 4 is divided into three zones: a sample receiving zone 6, a labelling zone 8, and a capture zone 10. An absorbent zone 12 which contacts the support matrix 4 is present. The absorbent zone 12 is constructed of a material which can absorb the biological fluid sample.

Analyte binding substances which are specific for the suspected analyte are impregnated within the sample receiving zone 6. The analyte binding substances mix with the fluid sample and form analyte/binding substance conjugates in the sample receiving zone 6 and flow laterally into the labelling zone 8.

Labelling complexes impregnated within the labelling zone 8 mix with the fluid sample and bind to the conjugates forming a labelled conjugate. The fluid sample continues lateral flow and transports the labelled conjugates to the capture zone 10 having an immobilized capture binding substance. The analyte in the labelled conjugates binds the capture binding substance in the capture zone 10 and is immobilized thereon. Excess fluid, unbound labelling complexes and the like continues lateral flow through the capture zone 10 into the absorbent zone 12. Analyte present in the fluid sample is determined by observing the accumulation of color from the dyed microorganisms in the capture zone 10.

Figure 2:
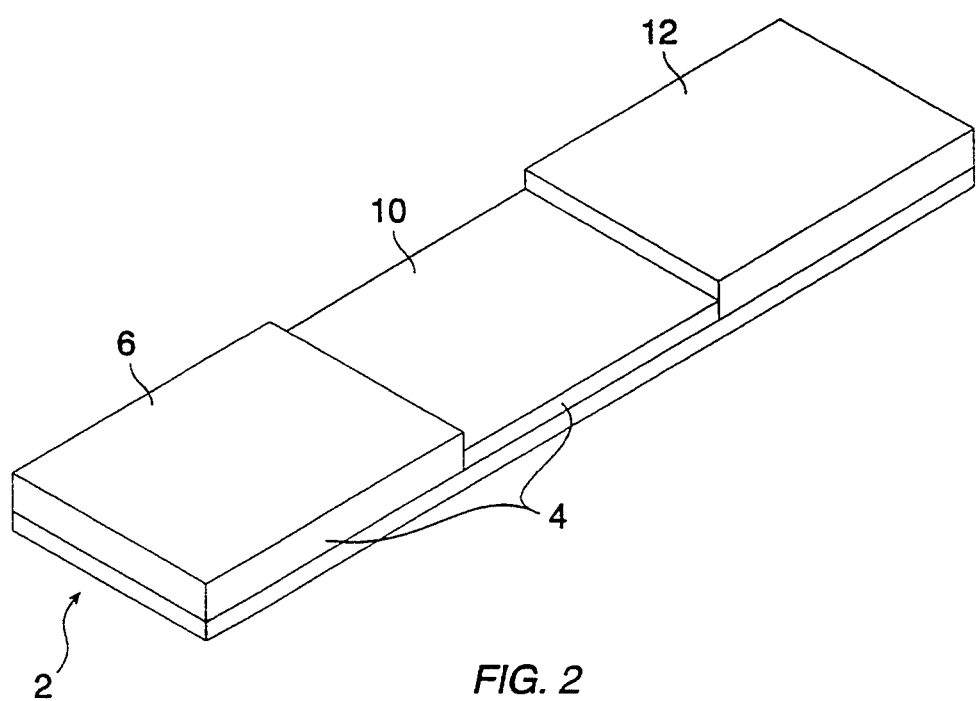
FIG. 2 illustrates a test article constructed in accordance with the principles of the present invention for the detection of analyte in a sample through the performance of competitive binding assays.

Referring now to FIG. 2, a test article 2 constructed in accordance with the principles of the present invention for the detection of analyte in a sample through the performance of competitive binding assays is illustrated. The test article 2 comprises a support matrix 4 capable of non-bibulous flow and an absorbent zone 12.

The support matrix 4 is divided into two zones: a sample receiving zone 6 and a capture zone 10. The capture zone 10 has a capture binding substance immobilized thereon. A labelled conjugate is bound to the capture binding substance. The labelled conjugate comprises the analyte bound to an analyte binding substance, which is in turn bound to a labelling complex containing a dyed microorganism. Thus, dyed microorganisms are retained in the capture zone 10.

When a fluid sample is placed on the sample receiving zone 6, the fluid flows laterally into the capture zone 10. Analyte present in the fluid will bind the capture binding substance and competitively displace the bound labelled conjugates. As the labelled conjugates are displaced, they flow laterally with the fluid to the absorbent zone 12. In this manner, analyte in the fluid sample causes the color intensity in the capture zone 10 to decrease.

The following examples are offered by way of illustration, not by way of limitation.

EXAMPLES

Example 1

This example demonstrates the effectiveness of test articles and methods of the present invention. Human chorionic gonadotropin (hCG) was detected in urine samples containing known amounts of hCG. The results demonstrate the sensitivity and rapidity of the present invention.

A seed lot of *S. aureus* (Cowan I strain ATCC 12598), in tryptic soy broth containing 20% glycerol and stored in liquid nitrogen, was used to grow an inoculum, 25 ml, in tryptic soy broth at 37° C. for 72 hr. on a rotator at 90 rpm. Five ml aliquots of inoculum were placed in 3 one-liter bottles containing 700 ml each of tryptic soy broth and grown for 48 hr. at 37° C. on a rotator at 90 rpm.

The resulting *S. aureus* were harvested in 50 ml conical tubes by centrifugation for 30 min. at 3000 rpm on a Sorvall RC-5B centrifuge. The supernatants were decanted and discarded. Pellets were washed by centrifugation in 50 ml conical tubes in a Sorvall RT 6000 rotor (3000 rpm for 30 min.) using 10 times the pellet volume of phosphate buffered saline ((PBS), 0.12M sodium chloride, 0.05M sodium phosphate, 0.02% sodium azide, pH 7.2). The cells were re-suspended to about 10% suspension in 1.5% formaldehyde (used to render the organisms non-infectious) in PBS and placed in a 50 ml conical tube and rotated for 1.5 hr. The resulting formaldehyde fixed cells were harvested by centrifugation (3000 rpm for 30 min.) in a Sorvall RT 6000 centrifuge. The cells were washed by re-suspension to about 10% in PBS and centrifugation at 3000 rpm for 30 min. The supernatant was discarded and the cells were re-suspended to about 10% in PBS. The cells were heat killed by incubation at 80° C. for 18 hr. in a water bath. The cells were placed on ice for one hour, after which they were collected by centrifugation (3000 rpm, for 30 min). The supernatant was discarded and the pellet re-suspended to about 10% in freshly prepared 0.5 mg/ml NaBH$_4$ in PBS. After 15 min. incubation at room temperature, the cells were collected by centrifugation (3000 rpm for 30 min). The supernatant was discarded and the cells were washed by centrifugation twice with PBS. The cells were suspended to 10% and washed once by centrifugation (3000 rpm for 30 min) with tris buffer, 50 mM, pH 8.0. Finally, the cells were suspended in tris buffer, 50 mM, pH 8.0 and stored at 4° C. A viability check was made by growing a loop of suspension streaked on blood agar medium for 48 hr. to confirm that the cells were killed.

*S. aureus* (9.5 ml with a solid density of 7.6%) was pelleted by centrifugation at 10,500 rpm in a Sorvall RC-5B centrifuge for 10 minutes in a 10 ml Corex tube. The pellet was suspended in 0.10M sodium bicarbonate sodium carbonate buffer, pH 9.5 and washed by centrifugation twice in the same buffer. The cell pellet was finally suspended in 8.74 ml of 0.10M sodium bicarbonate sodium carbonate buffer, pH 9.5. Cibacron brilliant red 3B-A (54 mg, Aldrich) was dissolved in the *S. aureus* suspension with rapid stirring. The resulting red suspension was distributed into 19×1.5 ml Eppendorf plastic capped tubes, 500 µl into each, and rotated end-over-end for 18 hr. The contents were pooled into a 30 ml Corex centrifuge tube and centrifuged at 10,500 rpm at 4° C. for 10 min. in a Sorvall RC-SB. The pellet was re-suspended in 19 ml 20% ethanol in tris, 50 mM, pH 8.0 and collected by centrifugation at 10,500 rpm at 4° C. for 10 min. The supernatant was discarded and the pellet was washed three more times by centrifugation until the supernatant was colorless. The pellet was re-suspended in tris, 50 mM, pH 8.0 and pelleted by centrifugation. Finally, the dyed S. aureus product was suspended in 3.78 ml tris, 50 mM, pH 8.0, to a solids density of 13.5% in suspension, and stored at 4° C.

Ninety five μl of Cibacron Brilliant Red 3B-A dyed S. aureus (13.5% suspension) was diluted into 265 μl of 10% polyvinylpyrrolidone in tris, 50 mM, pH 8.0. A 328 μl aliquot of diluted S. aureus was applied to a 1.8×4.8 cm piece of Sontara TM spunlaced 100% acrylic fiber (Dupont) backed with a mylar sheet using double-stick tape (444,3M). The Sontara TM impregnated with S. aureus was allowed to stand for 20 min. to allow the liquid containing microorganisms to spread evenly. The Sontara TM piece was placed in a freezer and frozen at −70° C. for 60 min. then lyophilized (Virtis Freezemobile 12) at 10 millitorr for 21 hr.

Mouse monoclonal anti-hCG, subclass 2a (9.44 mg/ml, 20 μl) was diluted into 3000 μl of 10 mg/ml methylated BSA in tris, 50 mM, pH 8.0. A 2846 μl aliquot was applied to a 7.0×10.7 cm piece of Sontara TM spunlaced 100% acrylic fiber (Dupont) backed with a mylar sheet using 3M Adhesive 444. The Sontara TM impregnated with antibody was allowed to stand for 20 min. to allow the liquid to spread evenly. The Sontara TM piece was placed in a freezer and frozen at −70° C. for 60 min. then lyophilized (Vertis Freezemobile 12) at 10 millitorr for 21 hr.

Rabbit F(ab')2 fragment of anti-hCG, 6.0 mg/ml, was loaded into a pen and spotted on a line on nitrocellulose (AE99, 8 μ pore size, Schleicher and Schnell) using a SE 780 X-Y plotter (Asea Brown Boveri) with a pen speed of 0.5 sec/cm. After air drying for 10 min., the spotted nitrocellulose was dipped into 10 mg/ml methylated BSA in tris, 50 mM, pH 8.0 and incubated submerged for 15 min. to block the remainder of the nitrocellulose to render it non-bibulous. Next, it was blotted dry between two pieces of blotter absorbent (ED 939, Ahlstrom) for 5 min., then dried at 45° C. for 10 min. in a forced air oven. The dried nitrocellulose was backed with a mylar sheet coated with double-stick adhesive tape (444,3M). It was stored in a dry room at 13% relative humidity.

Test strips, 3 mm wide, were assembled from the Sontara TM membranes containing dyed S. aureus used as a labelling zone, from Sontara TM membrane containing mouse monoclonal anti-hCG used as the sample receiving zone, and from the nitrocellulose capture zone with rabbit F (ab')2 fragment of anti-hCG by the method disclosed in co-pending patent application U.S. Ser. No. 07/847,487 "Red Blood Cell Separation Means for Specific Binding Assays".

Thirty μl samples of urine calibrators prepared in pooled male urine were applied to the sample receiving zones of the 3mm hCG test strips. The time of the first visible pink line on nitrocellulose capture zone was recorded (Table 1).

TABLE 1

| Calibrator (mIU/ml) | Time of First Visible Signal |
|---|---|
| Experiment A | |
| 0 | none observed |
| 0 | none observed |
| 200 | 1 min. 53 sec. |
| 200 | 2 min. 6 sec. |
| 1000 | 1 min. 8 sec. |
| 1000 | 1 min. 6 sec. |
| Experiment B | |
| 0 | none observed |
| 0 | none observed |
| 150 | 10 min. 48 sec. |
| 150 | 11 min. 31 sec. |
| 1000 | 1 min. 40 sec. |
| 1000 | 1 min. 45 sec. |

Experiment A capture zone was located 4 mm from the Sontara TM labelling zone containing dyed S. aureus.

Experiment B capture zone was located 9 mm from the Sontara TM labelling zone containing dyed S. aureus.

The results demonstrate that the test articles and methods of the present invention employing dyed S. aureus as a label provide a sensitive and accurate means for detecting analytes in immunoassays.

Example 2

This example demonstrates the construction of an immunoassay test article employing dyed E. coli as labels in a visual immunoassay for the detection of hCG in urine samples.

E. coli are grown aerobically in nutrient broth (Difco Laboratories, Detroit Mich.), at 37° C. for 72 hours on a rotator. The cultures are then transferred to fresh medium in a ratio of 1:25. The bacteria are grown for an additional 24 hours at 37° C. on a rotator. An aliquot of the bacteria-containing medium is reserved for monoclonal antibody production described below.

The cultures are then harvested by centrifugation. The supernatants are decanted and discarded. The cells are heat killed, cooled on ice, and then collected by centrifugation. Pellets are washed using 10 times the pellet volume of phosphate buffered saline ((PBS), 0.12M sodium chloride, 0.05M sodium phosphate, 0.02% sodium azide, pH 7.2). The E. coli are re-suspended to about 10% suspension in 1.5% formaldehyde in PBS, placed in a 50 ml conical tube and rotated for 1.5 hr. The resulting formaldehyde fixed cells are harvested by centrifugation. The fixed cells are washed by re-suspension to about 10% in PBS and centrifuged. The supernatant is discarded and the cells re-suspended to about 10% in PBS. The supernatant is discarded and the pellet re-suspended to about 10% in freshly prepared 0.5 mg/ml NaBH4 in PBS. After incubation the cells are collected by centrifugation. The supernatant is discarded and the cells washed by centrifugation twice with PBS. The cells are resuspended to 10% and washed once by centrifugation in PBS. Finally, the cells are suspended in tris buffer, 50 mM, pH 8.0 and stored at 4° C. A viability check is made by growing a loop of suspension streaked on nutrient medium for 48 hr. to confirm that the cells have been killed.

The fixed E. coli are pelleted by centrifugation and suspended in 0.10M sodium bicarbonate sodium carbonate buffer, pH 9.5. Remazol Brilliant Blue R (Aldrich) is dissolved in the cell suspension. The resulting suspension is incubated with rotation for 12 hours. The cells are pelleted by centrifugation and re-suspended in 19 ml of a solution of 20% ethanol in tris, 50 mM, pH 8.0. The supernatant is discarded and the pellet washed by centrifugation until the supernatant was colorless. The pellet was re-suspended in tris, 50 mM, pH 8.0 and pelleted by centrifugation. Finally, the dyed *E. coli* are suspended in 4.5 ml tris, 50 mM, pH 8.0, to a density of 11.0% solids suspension, and stored at 4° C.

Murine monoclonal antibodies to *E. coli* are prepared by standard techniques as described in Harlow and Lane, *Antibodies, A Laboratory Manual*, Cold Spring Harbor Laboratory, Cold Spring Harbor N.Y., previously incorporated herein by reference. The reserved aliquot of microorganisms provides antigens for immunization of the mice or other animals. The harvested antibodies are then mixed in solution with excess purified Staphylococcal protein A (SPA). The resulting antibody/SPA complex is mixed with the dyed *E. coli*. The antibodies bind the *E. coli* producing a dyed particle linked to SPA. The dyed E coli linked to SPA is separated from unbound antibody and SPA by centrifugation.

The dyed SPA linked *E. coli* are suspended in 10% polyvinylpyrrolidone in tris, 50 mM, pH 8.0. A 456 ml aliquot of the *E. coli* is applied to a 2.0×6.0 cm piece of Sontara TM spunlaced 100% acrylic fiber (Dupont) backed with a mylar sheet using double-stick tape (444,3M). The Sontara TM impregnated with *E. coli* is incubated for 20 min. to allow the liquid to spread evenly. The Sontara piece is placed in a freezer and frozen at −70° C. for 60 min. then lyophilized (Virtis Freezemobile 12) at 10 millitorr for 21 hr.

Mouse monoclonal anti-hCG, is applied to a 7.0×10.7 cm piece of Sontara TM and lyophilized as explained in Example 1 above for use as a sample receiving zone.

Rabbit anti-hCG F(ab')$_2$ fragments (6.0 mg/ml) are loaded into a pen and spotted on a line on nitrocellulose (AE99, 8 μ pore size, Schleicher and Schnell) using a SE 780 X-Y plotter (Asea Brown Boveri) with a pen speed of 0.5 sec/cm. After air drying for 10 min., the spotted nitrocellulose is dipped into 10 mg/ml methylated BSA in tris, 50 mM, pH 8.0 and incubated submerged for 15 min. to block the remainder of the nitrocellulose. Next, it is blotted dry between two pieces of blotter absorbent (ED 939, Ahlstrom) for 5 min., then dried at 45° C. for 10 min. in a forced air oven. The dried nitrocellulose is backed with a mylar sheet coated with double-stick adhesive tape (444,3M). It was stored in a dry room at 13% relative humidity.

Test strips, 3 mm wide, are assembled from the Sontara TM membranes containing dyed *E. coli* as a labelling zone, the Sontara TM membrane containing mouse monoclonal anti-hCG as the sample receiving zone, and from the nitrocellulose capture zone with rabbit F (ab')$_2$ fragment of anti-hCG by the method disclosed in co-pending patent application U.S. Ser. No. 07/847,487 "Red Blood Cell Separation Means for Specific Binding Assays" (now abandoned).

Example 3

This example demonstrates the preparation of test articles for the detection of carcinoembryonic antigen in serum. The test articles employ dyed Group C Streptococcus as visual labels in the assays.

Group C streptococcus cells are grown in TYT-glucose medium at 37° C. The cells are harvested by centrifugation and washed by two cycles of centrifugation and suspension of the pellet in 10 mM Tris-0.15M NaCl adjusted to pH 7.5 with HCl. The cells are heat killed and viability checked by growing a streak on blood agar.

After confirming that the cells are non-viable, the cells are washed twice by centrifugation and resuspended in a solution of 0.10M sodium bicarbonate sodium carbonate buffer, pH 9.5. Cibacron Brilliant Red 3B-A is dissolved in the solution and the cells are incubated for 18 hours. The cells are pelleted by centrifugation and re-suspended in 19 ml 20% ethanol in tris, 50 mM, pH 8.0. The supernatant is discarded and the pellet washed by centrifugation until the supernatant is colorless. The pellet is re-suspended in tris, 50 mM, pH 8.0 and pelleted by centrifugation. Finally, the dyed cells are suspended in 4.0 ml tris, 50 mM, pH 8.0, to a density of 12.5% solids in suspension, and stored at 4° C. The dyed Group C streptococcus are washed twice by centrifugation in PBS and resuspended in 3% methylated BSA/PBS with 0.02% sodium azide at a concentration of 0.06% solids.

A nitrocellulose membrane, 8 μ pore size, is prepared as follows. The membrane is affixed to a chart recorder and anti-CEA Fab fragments dispensed in a line at 10 mg/ml in 50 mM Tris, pH 8.0. The anti-CEA line defines the capture zone of the device.

The dyed cell suspension is applied to the membrane about 1 cm parallel to the anti-CEA line. Mouse anti-CEA IgG antibody is applied to the membrane 1 cm parallel to the dyed cell suspension on the side opposite to the placement of the anti-CEA Fab fragment line. The nitrocellulose membrane is then placed in a tray containing 50 mM Tris maleate buffer, pH 7.0, containing 5 mg/ml mBSA for 5 minutes at room temperature. The membrane is blotted to remove excess liquid, dried in a convection oven at 45° C. for 5 minutes, and stored in a desiccator at room temperature until assembly of the device. The membranes are then cut into 10×7.5 mm rectangles, each containing the anti-CEA antibody line (sample receiving zone), the dyed Streptococcus C line (labelling zone), and the anti-CEA Fab line (capture zone).

Although the foregoing invention has been described in some detail by way of illustration and example, for purposes of clarity and understanding, it will be obvious that changes and modifications may be practiced within the scope of the appended claims.

What is claimed is:

1. A test article for the detection of an analyte in a sample, comprising:

a support matrix defining a flow path; a labelling complex for labelling analyte/analyte binding substance, complex, wherein said labelling complex is impregnated within the support matrix in a labelling zone, and wherein the labelling complex comprises a visibly-dyed killed bacterium comprising a naturally occurring cell surface receptor as a specific labelling binding substance; and a capture zone located along said flow path downstream from said labelling zone and having a capture binding substance specific for said analyte immobilized therein.

2. The test article as in claim 1, wherein the bacterium is *Staphylococcus aureus* and the specific labelling binding substance is protein A.

3. The test article as in claim 1, wherein the labelling complex is lyophilized within the support matrix.

4. The test article as in claim 1, wherein the support matrix conducts non-bibulous flow of a liquid sample.

5. The test article as in claim 1, wherein the support matrix conducts bibulous flow of a liquid sample.

6. The test article as in claim 1, wherein the support matrix is a fabric composed of a polyester, an acrylonitrile copolymer, rayon, glass fiber, cellulose, or blends thereof.

7. The test article as in claim 6, wherein the fabric has been treated with a blocking agent to render the fabric non-bibulous.

8. The test article as in claim 1, wherein the bacterium is Streptococcus group C or G and the specific labelling binding substance is protein G.

9. A test article comprising:
a support matrix defining a flow path;
a sample receiving zone located along said flow path and comprising an analyte binding substance specific for an analyte impregnated therein, wherein an analyte/analyte binding substance complex is formed by application of the analyte to the sample receiving zone;
a labelling zone located along said flow path downstream from said sample receiving zone, which labelling zone comprises a labelling complex impregnated therein to label said analyte for detection, wherein said labelling complex comprises a visibly-dyed killed bacterium comprising a naturally occurring receptor as a labelling binding substance specific for binding said complex on its cell surface; and
a capture zone located along said flow path downstream from said labelling zone, which capture zone comprises a capture binding substance specific for said analyte immobilized therein, to immobilize the labelled analyte.

10. The test article as in claim 9, wherein the analyte binding substance within the sample receiving zone is an IgG antibody specific for the analyte.

11. The test article as in claim 10, wherein the labelling complex within the labelling zone is dyed Streptococcus group C or G and the specific labelling binding substance is protein G.

12. The test article as in claim 10, wherein the antibody is anti-hCG.

13. The test article as in claim 10, wherein the labelling complex within the labelling zone is dyed *Staphylococcus aureus* and the labelling binding substance is protein A.

14. The test article as in claim 13, wherein the capture binding substance within the capture zone is an antibody or antibody fragment specific for the analyte and lacking an $F_C$ region so that it will not bind protein A.

15. The test article as in claim 9, wherein the analyte binding substance is lyophilized within the sample receiving zone.

16. The test article as in claim 9, wherein the labelling complex is lyophilized within the labelling zone.

17. The test article as in claim 9, wherein the capture binding substance is dried but not lyophilized within the capture zone.

18. The test article as in claim 9, wherein the support matrix conducts non-bibulous flow of a liquid sample.

19. The test article as in claim 9, wherein the support matrix conducts bibulous flow of a liquid sample.

20. The test article as in claim 9, wherein the support matrix is a fabric composed of a polyester, an acrylonitrile copolymer, rayon, glass fiber, cellulose, or blends thereof.

21. The test article as in claim 20, wherein the fabric has been treated with a blocking agent to render the fabric non-bibulous.

22. An assay for determining the presence of an analyte in a sample, comprising:
applying the sample to the sample receiving zone of a test article as in claim 9; and
observing accumulation of labelling complexes in the capture zone.

23. The assay as in claim 22, wherein sample flow through the capture zone results in binding of the analyte to the capture binding substance, whereby label accumulates in the capture zone in proportion to the amount of analyte in the sample.

24. The assay as in claim 22, wherein the dyed bacterium is *Staphylococcus aureus* and the specific labelling binding substance is protein A.

25. The assay as in claim 22, wherein the dyed bacterium is Streptococcus group C or G and the specific labelling binding substance is protein G.

26. A method for preparing a test article, said method comprising impregnating a labelling complex within a support matrix, wherein the labelling complex comprises a killed visibly-dyed bacterium comprising a naturally occurring receptor as a specific labelling binding substance on its cell surface, and immobilizing a capture binding substance in a capture zone.

27. The method as in claim 26, wherein the labelling complex is lyophilized within the support matrix.

28. The method as in claim 26, wherein the dyed bacterium is *Staphylococcus aureus* and the specific labelling binding substance is protein A.

29. The method as in claim 26, wherein the labelling complex is lyophilized within the support matrix.

30. The method as in claim 26, wherein the support matrix conducts non-bibulous flow of a liquid sample.

31. The method as in claim 26, wherein the support matrix conducts bibulous flow of a liquid sample.

32. The method as in claim 26, wherein support matrix is a fabric composed of a polyester, an acrylonitrile copolymer, rayon, glass fiber, cellulose, or blends thereof.

33. The method as in claim 32, wherein the fabric has been treated with a blocking agent to render the fabric non-bibulous.

34. The method as in claim 26, wherein the dyed bacterium is Streptococcus group C or G and the specific labelling binding substance is protein G.

* * * * *